United States Patent [19]

Akerson

[11] Patent Number: 5,331,967
[45] Date of Patent: Jul. 26, 1994

[54] TRACHEAL INTUBATION MONITORING APPARATUS AND METHOD

[75] Inventor: Steve H. Akerson, Puntarenas, Costa Rica

[73] Assignee: Playa de los Vivos S.A., Costa Rica

[21] Appl. No.: 15,405

[22] Filed: Feb. 5, 1993

[51] Int. Cl.$^5$ .............................................. A61B 5/08
[52] U.S. Cl. .................. 128/716; 128/207.14
[58] Field of Search ............... 128/716, 720, 653.1, 128/773, 200.26, 903, 207.14, 207.15, 207.16, 207.18; 324/643; 73/579, 586, 587, 589, 591, 592, 645, 149, 290 R, 290 V, 294, 301, 307

[56] References Cited

U.S. PATENT DOCUMENTS

| | | |
|---|---|---|
| 2,584,128 | 2/1952 | Hildyard . |
| 2,932,818 | 4/1960 | Lubkin . |
| 2,990,543 | 6/1961 | Rod . |
| 3,050,720 | 8/1962 | Rich . |
| 3,572,119 | 8/1969 | Bak .................... 73/290 R |
| 3,798,959 | 3/1974 | Bowles et al. ............... 73/579 X |
| 3,938,072 | 2/1976 | Baird et al. . |
| 3,960,007 | 6/1976 | Swenson . |
| 4,095,474 | 6/1978 | Hancock et al. . |
| 4,212,201 | 7/1980 | Hirsch et al. . |
| 4,325,255 | 4/1982 | Howard et al. ............ 73/290 V X |
| 4,326,416 | 4/1982 | Fredberg ................ 128/720 X |
| 4,431,005 | 2/1984 | McCormick ........... 128/653.1 X |
| 4,458,530 | 7/1984 | Bastida ..................... 73/290 R |
| 4,630,606 | 12/1986 | Weerda et al. . |
| 4,653,327 | 3/1987 | Varterasian et al. ............... 73/579 |
| 4,729,245 | 3/1988 | Hansman, Jr. ............... 73/149 X |
| 4,790,183 | 12/1988 | Pfost et al. ................. 73/290 V |
| 4,864,856 | 9/1989 | Ichikawa et al. . |
| 4,887,068 | 12/1989 | Umehara ................. 73/308 X |
| 4,949,716 | 8/1990 | Chenoweth . |
| 5,027,655 | 7/1991 | Sweet . |
| 5,128,656 | 7/1992 | Watanabe ................ 73/290 V X |

FOREIGN PATENT DOCUMENTS

| | | |
|---|---|---|
| 129788 | 3/1959 | U.S.S.R. . |
| 214014 | 3/1967 | U.S.S.R. . |
| 309699 | 6/1970 | U.S.S.R. . |
| 401351 | 10/1978 | U.S.S.R. . |
| 2068735 | 8/1981 | United Kingdom . |

OTHER PUBLICATIONS

"Mechanical Response of Lungs at High Frequencies", J. J. Fredberg et al., May 20, 1978, *Journal of Biomechanical Engineering*.

"Canine Pulmonary Input Impedance Measured by Transient Forced Oscillations" J. J. Fredberg et al.; *Journal of Biomechanical Engineering*, May 1978.

*Primary Examiner*—Lee S. Cohen
*Assistant Examiner*—Samuel Gilbert
*Attorney, Agent, or Firm*—Baker & Botts

[57] ABSTRACT

A method and apparatus for monitoring and indicating whether a tracheal tube is located in the trachea or esophagus during an endotracheal intubation of a human or animal is disclosed. In a calibration mode, the resonant frequency of the tube is determined by generating a signal at a plurality of frequencies and finding the signal which propagates with the greatest amplitude. This indicates the resonant frequency. When the tube is inserted into the patient, the resonant frequency of the system shifts, thus the amplitude of the signal changes. Based on known characteristics of the trachea and esophagus, the amount of change is dictated by whether the tube has been inserted into the trachea or esophagus. Alternatively, the device can continually determine the resonant frequency and use this to monitor the level of liquid in a tank.

8 Claims, 3 Drawing Sheets

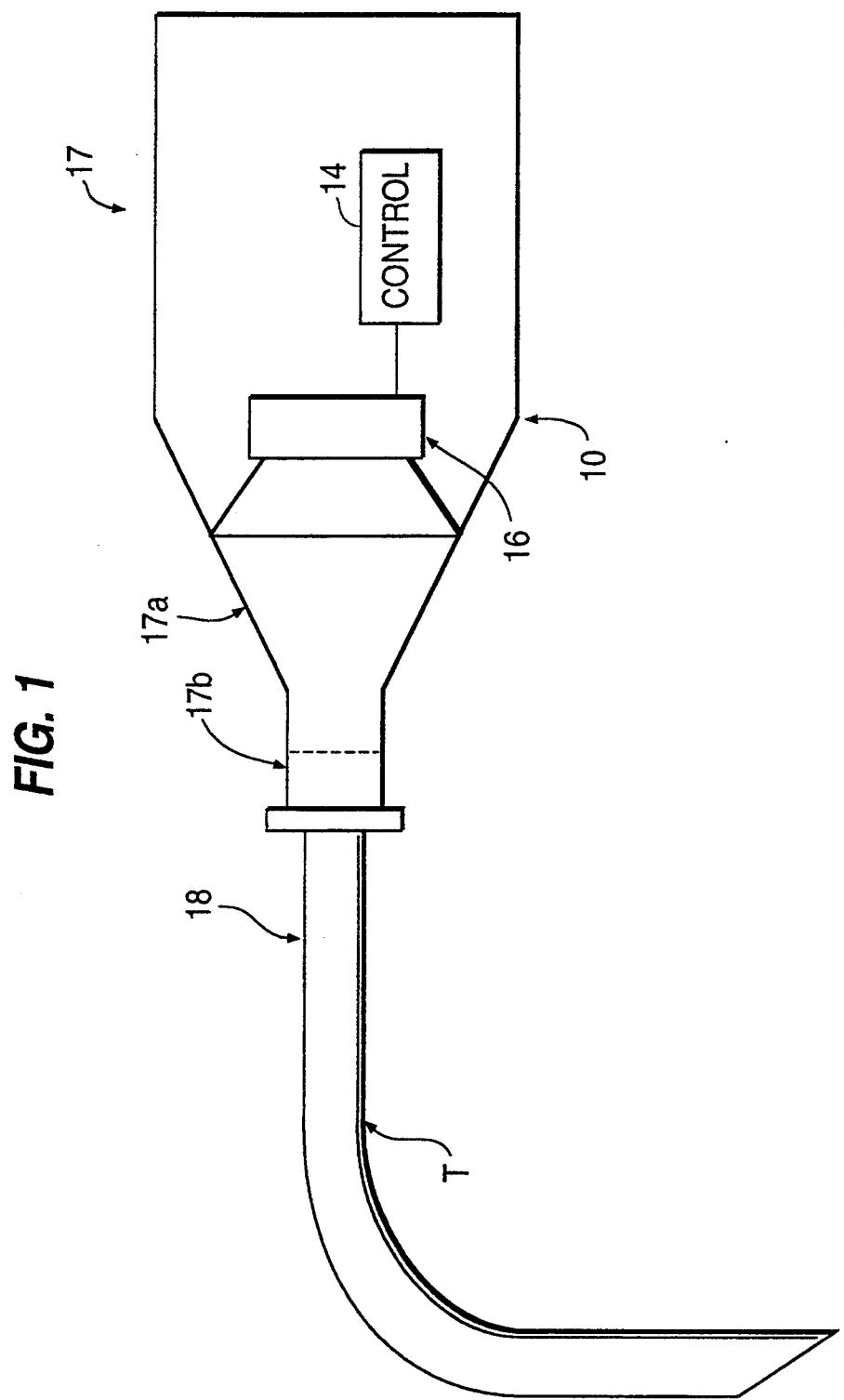

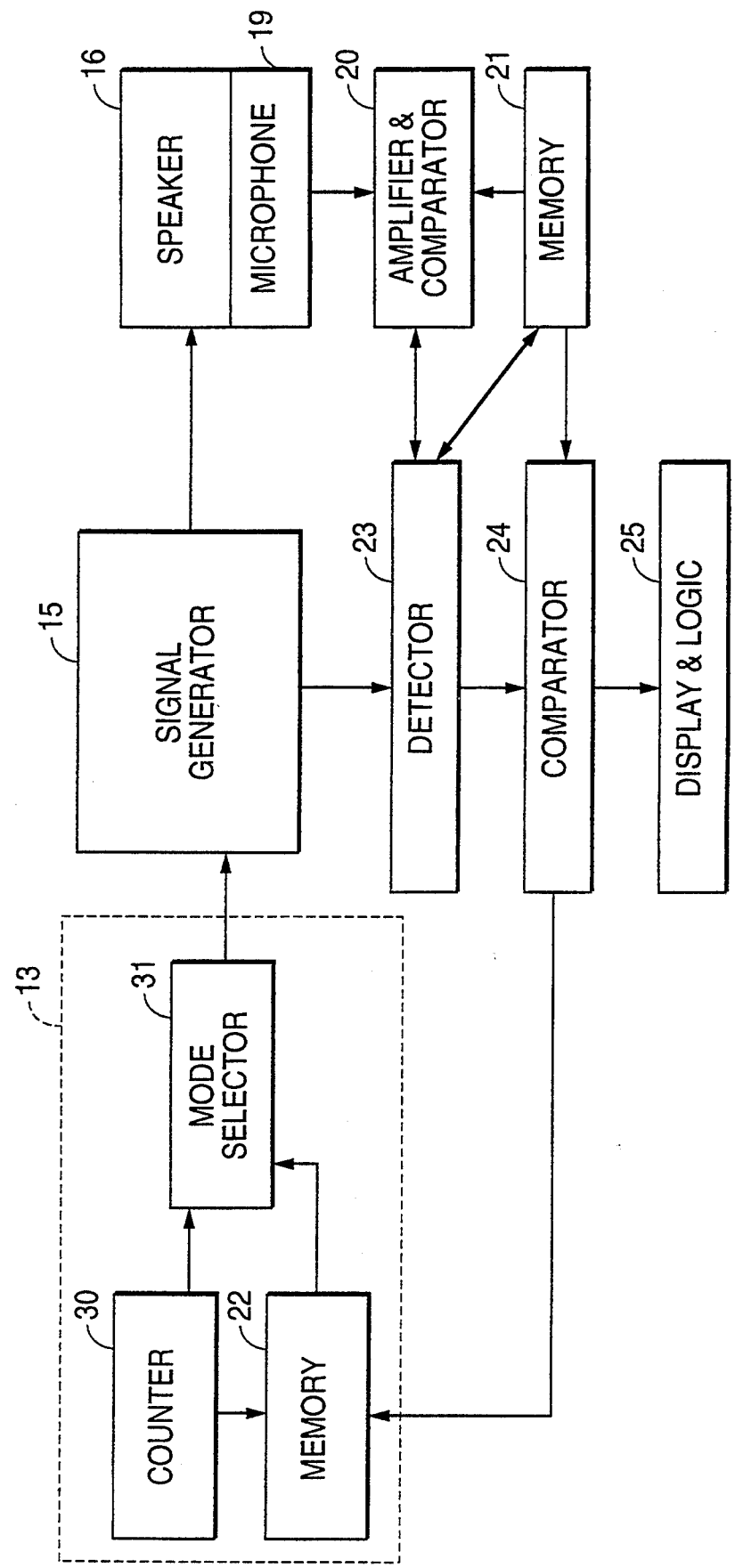

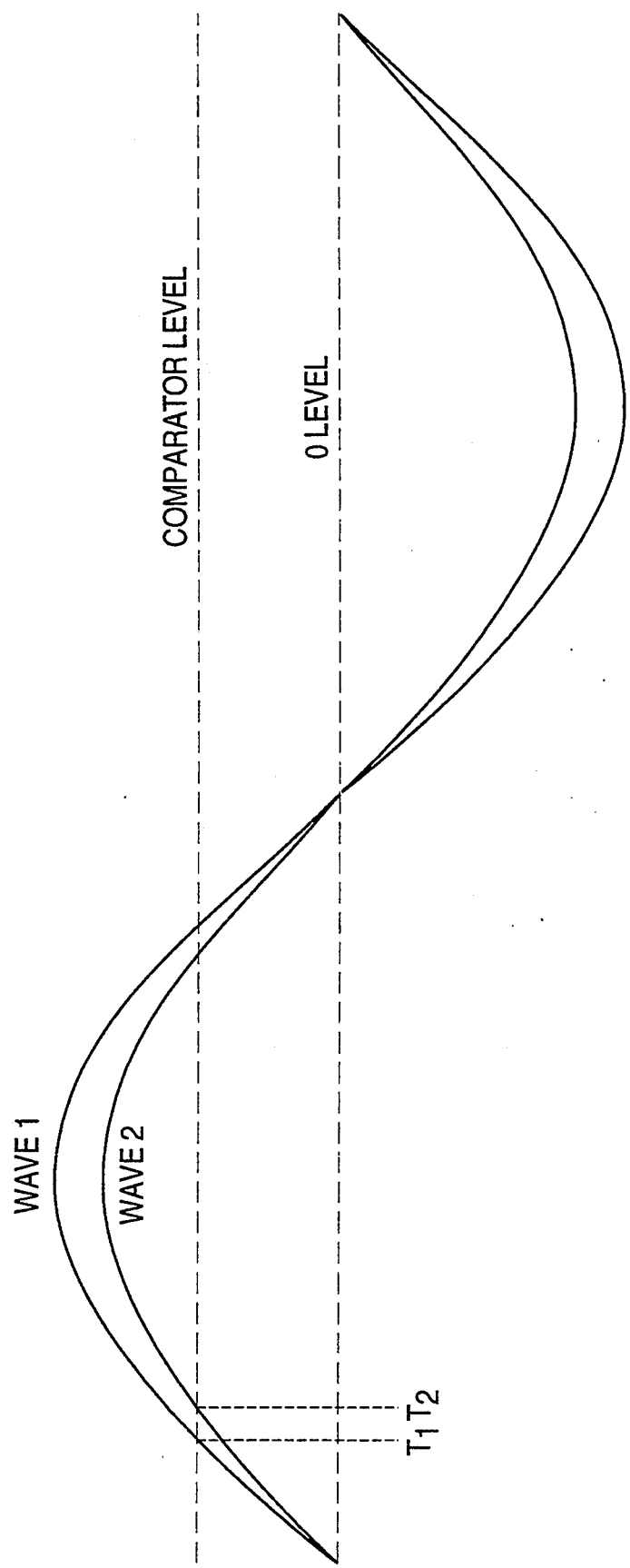

5,331,967

TRACHEAL INTUBATION MONITORING APPARATUS AND METHOD

FIELD OF THE INVENTION

The invention relates generally to a monitoring apparatus and method and more specifically, to a tracheal tube monitoring apparatus and method.

BACKGROUND OF THE INVENTION

For many surgical procedures, a patient is anesthetized and thereby rendered unconscious. In this condition, the patient is typically paralyzed and cannot breathe. Therefore, it is common to perform an endotracheal intubation whereby a tube, connected to an artificial breathing machine, is inserted into the patient's trachea. However, sometimes the anesthesiologist errs and inserts the tube into the esophagus. In the past, there was no way to know whether the tube was incorrectly inserted until the breathing machine was hooked up. Even then, it typically took several breaths and considerable expertise and expensive equipment to determine if the tube was in the esophagus. If it was, the intubation had to be attempted again. If the error was repeated a number of consecutive times, the patient could die.

A number of techniques have been developed to determine whether an intubation attempt is successful. For example, one currently employed technique uses capnography to measure intidal carbon dioxide levels. However, this equipment is very expensive and often requires several breaths before a stable reading is given. These are obviously undesirable drawbacks.

SUMMARY OF THE INVENTION

In view of the foregoing, it is an object of the present invention to overcome these and other drawbacks of the prior art.

Specifically, it is an object of the present invention to quickly, reliably and economically determine whether a tracheal tube is properly located in a patient's trachea.

It is another object of the invention to monitor a cavity to determine characteristics of the cavity. For example, it is an object to determine the level of liquid in a container.

In order to accomplish these and other objects of the present invention, there is provided a monitoring apparatus which includes a transducer that transmits sound waves of various frequencies into a tube. The characteristics of the tube will affect characteristics of the sound waves. For example, depending on the frequency of the sound waves, the tube will affect the amplitude of the sound waves. When the tube end is merely surrounded by air, the tube will have certain affects on the sound waves. If the tube is inserted into a cavity, e.g. a trachea, different affects on the sound waves will occur. If the tube is inserted into an esophagus, which tends to block or plug the end of the tube, then another affect will occur. Thus, by detecting characteristics of the sound waves at, for example, a resonant frequency of the tube surrounded by air, the monitoring device can determine whether the tube has been inserted into a cavity based on a measurable change in a characteristic of the sound wave, for example, the amplitude. This technique may be used, for example to determine whether a tube is located in the trachea or the esophagus. While other characteristics may be measured, for simplicity, the sound wave amplitude will be used as an example.

Typically, any cavity has at least one resonant frequency. In that cavity, sound waves of that frequency require less energy to reach a given amplitude than sound waves of other frequencies. Alternatively, for a given energy, the amplitude of a sound wave at a resonant frequency will be a maximum amplitude for those conditions. According to a preferred embodiment of the present invention, the monitoring apparatus is connected to a tube and is operated in a calibration mode to determine a resonant frequency of the tube and whatever is connected to the tube. For example, in the calibration mode, the tube may be surrounded simply by air. By generating a sound wave based on a constant current sine wave, the amplitude of the sound wave at the resonant frequency can be determined and a signal representative of that amplitude may be stored. In a monitoring mode, the monitoring device produces a signal at that resonant frequency and continuously measures the amplitude of the generated sound wave. When the tube is inserted into the trachea or esophagus, a detectable difference is measured (as compared with when the tube is surrounded by air), and an indication of the difference is provided. For example, as compared with the amplitude of the sound waves at resonant frequency when the tube is surrounded by air, it has been found that the resonant frequency amplitude decreases by less than about 5% when the tube is inserted into a trachea, but decreases by about 20% when inserted into the esophagus. Thus, by measuring the amplitude of the sound wave and comparing the measured amplitude to predetermined threshold levels, it can be determined whether the tube is inserted into the trachea or esophagus. An indication of the decrease can be provided to signal a correct or incorrect insertion of the tube. For example, a digital readout or other type of display can be generated to provide a precise measure of the change in amplitude for an anesthesiologist to interpret or various colored lights can be illuminated to indicate a correct or incorrect insertion. Various alternative methods may also be used. For example, in the calibration mode, the tube may be plugged, simulating insertion into the esophagus, rather than merely being surrounded by air. This and other various modifications will be apparent to one of ordinary skill in the art.

The indication may be in a variety of forms. For example, digital displays or illumination of colored lights are just two ways of providing an indication. For example, if during the calibration mode, the device is hooked up to an open tracheal tube (surrounded by air), and later the end is plugged (for example, by inserting it into the esophagus), then a measurable difference in sound waves is detected which may turn on a red light. Alternatively, if a plugged tracheal tube is used during calibration, then unplugging it will make a measurable difference which turns a red light on. If the tube later becomes plugged again, i.e., it is inserted into the esophagus, a green light will turn on.

According to one embodiment, when the light is green, it indicates the system is as it was when it was turned on. If the system changes beyond a preset threshold the light turns red. Alternatively, if it changes by more than one-half of the preset threshold, a yellow light may be turned on. These light changes are instantaneous giving the user feedback on placement of the tube while insertion is being attempted. Currently, anesthesiologists must insert the tube, hook up the respirator, and wait for several breaths while listening for gurgling sounds in the stomach or monitoring the in-tidal carbon dioxide content with capnography equipment. If it is suspected that the tube is indeed in the esophagus, then the anesthesiologist must start over again. In this same amount of time which represents one "trial and error attempt" with current methodology, an anesthesiologist could try dozens of attempts with the present invention.

According to another embodiment, the present invention may be used to continuously determine the resonant frequency of a cavity or container and use this to information either to drive a digital display or to cause a visual indication of the state of the cavity or container. For example, this technique may be used to determine the level of liquid in a container.

BRIEF DESCRIPTION OF THE DRAWINGS

FIG. 1 is a schematic illustration of a monitoring apparatus according to one embodiment of the present invention.

FIG. 2 is a block diagram of one embodiment of processing circuitry which may be used with the present invention.

FIG. 3 is a schematic illustration of two waves to illustrate an example of how signal changes may be detected.

DETAILED DESCRIPTION OF THE PREFERRED EMBODIMENTS

FIGS. 1 and 2 show one example of a monitoring apparatus, generally indicated by reference numeral 10. The monitoring apparatus 10, which is connected to a tube T, comprises a control system 14. As shown, for example in FIG. 2, the control system 14 comprises a signal generator 15, for example, a sine wave generator that is capable of generating a constant current sine wave with a digitally controlled frequency. The signal generator is controlled by an input circuit 13. The input circuit 13 comprises a counter 30, a memory 22 and a mode selector 31. The operation of the input circuit is described below. Generally speaking, however, the input circuit controls the frequency of the signal generated by the signal generator 15. The output of the signal generator 15 drives a first transducer, for example, a speaker 16 mounted in a funnel-shaped portion 17a of monitor housing 17. Preferably, the funnel-shaped portion 17a ends in a tube fitting 17b which is sized to be connected to a tube T (e.g. a tracheal tube). For use with a tracheal tube, the tube fitting 17b may be approximately 15 mm in diameter or otherwise sized to be connected to the tube. A second transducer, for example, a microphone 19 is operatively positioned (e.g. in the funnel-shaped portion 17a) to monitor the amplitude of the signal generated by signal generator 15. Alternatively, the signal may be measured by monitoring the voltage drop across the first transducer (e.g. to determine a change in its impedance since it is driven by a constant current source). Depending on what is connected to the tube, the signal will have different characteristics (e.g. amplitudes).

In operation, the monitoring device is operable in a plurality of modes under control of mode selector 31. For example, the device is preferably first operated in a calibration mode to determine the resonant frequency of the tube T and whatever is connected to it. To accomplish this, the frequency of the signal produced by signal generator 15 is stepped through a plurality of frequencies under control of the input circuit 13. When the frequency approaches the resonant frequency, the amplitude of the signal detected by the second transducer increases dramatically. By measuring the signal amplitude at a plurality (e.g. 256) different frequencies, the frequency that produces the highest amplitude voltage is picked as the operating (resonant) frequency. The amplitudes (or voltage level) corresponding to this signal are then stored in a first memory (e.g. memory 21) and the frequency is stored in a second memory (e.g. memory 22). These stored values are used as reference values during operation in the manner described below.

According to one embodiment of the invention, when the monitoring apparatus 10 is turned on, the mode selector 31 is switched to select the calibration mode (manually or automatically). According to one embodiment, in the calibration mode, the counter 30 sequentially steps the signal generator 15 through a plurality (e.g. 256) different frequencies. For each frequency, the signal generator 15 generates an output signal, for example, a constant current sine wave having the selected frequency. This output signal drives a first transducer, e.g. speaker 16, to cause a second signal, for example, a sound wave to be propagated through the tube T. The amplitude (or other characteristic(s)) of the sound wave is detected either by measuring the voltage drop across the speaker itself or by using a second transducer, e.g. a microphone 19. In either case, the amplitude signal is amplified and compared to a preset level in amplifier and comparator 20. At each frequency, the detected amplitude signal is compared with a stored signal (initially zero) to determine if it is the highest amplitude. If it is, the amplitude level is stored in a first memory 21 and its corresponding frequency is stored in memory 22. After counter 30 has caused the signal generator to step through all of the predetermined plurality of frequencies, the first and second memories (21, 22) will contain the resonant frequency and the amplitude of the sound wave at the resonant frequency. Then, the mode selector 31 is switched (manually or automatically) to a monitoring mode. In the monitoring mode, the signal generator continuously produces a signal having the frequency stored in memory 22 (i.e. the resonant frequency determined in the calibration mode). The characteristic(s) of the sound wave produced by speaker 16 (e.g. its amplitude) is monitored by the second transducer, and this characteristic is compared to the stored characteristic (e.g. the amplitudes stored in memory 21).

A comparator 24 (e.g. a digital comparator) may be used for making the comparison. According to one embodiment, the comparator operates to compare the measured amplitude with that stored in memory 21. If the measured amplitude is below a predetermined threshold (e.g. approximately 95% of the reference amplitude), the comparator 24 generates a first signal indicating the tube is in the trachea. If the signal is below a second predetermined threshold (e.g. 80–90% of the reference amplitude), a second signal is generated indicating the tube is in esophagus.

For example, one way to compare the ever changing sensed level is to detect the time or phase angle (for example with phase angle detector 23) at which the sensed signal crosses a preset level and to compare this (e.g. in digital comparator 24) to the stored signal values. The smaller the signal amplitude, the later it will cross this level (see, for example, FIG. 3). The difference between time $T_1$ and $T_2$ (or phase angle) will give an indication of how much the level of the sound has decreased. The monitoring apparatus 10 may be preprogrammed such that the calibrated level is used as a reference value to which the detected signals are compared.

Due to the well known characteristics of the trachea and esophagus, insertion of the tube into the trachea causes the detected amplitude to drop by less than about 5%, whereas insertion of the tube into the esophagus causes the detected amplitude to drop by about 10-20%. Therefore, by storing the amplitude of the reference level ($A_R$) in memory 21 and comparing the detected amplitudes with predetermined threshold values approximately equal to $A_R$; 0.95 $A_R$; and 0.85 $A_R$ (or other desired values), it can be determined whether the tube has been inserted into the trachea or esophagus. Of course, other reference levels may be preferred for this or other uses of the monitoring apparatus. Preferably, the display and logic circuit 25 causes an appropriate indication upon detection of insertion of the tube into the trachea or esophagus. This information can be displayed directly or can drive logic that will operate different colored lights.

Since the device "self calibrates" when it is turned on it automatically compensates for different sizes of tubes and other devices which may be connected to the tube, for example, bacteria filters, right angle adapters, flexible hoses, etc.

Alternatively, the monitoring device can be operated in a continuous search mode by selection of this mode via mode selector 31. In this mode, the monitoring device continuously searches for the resonant frequency of the tube (and what it is connected to) and indicates changes in the resonant frequency with a colored light or a digital readout. This mode may be used to measure the resonant frequency of a cavity continuously and be used, for example, as a tank level gauge by inserting the tube into a tank containing fluid. As the level of the fluid changes, so too will the resonant frequency. For example, the resonant frequency would be a function of the volume of air in the tank. This liquid level monitoring device may be provided which does not contact the liquid. This device could be used, for example, for fuel tanks, water tanks, waste systems and hazardous chemical tanks. Such a device is very reliable and easy to install. Moreover, it would enable one monitor to measure the level in several tanks.

In this mode, the counter 30 continuously steps the signal generator through a plurality of different frequencies but otherwise operates in a manner similar to the foregoing embodiment(s), and the display 25 displays the resonant frequency directly or the drive logic causes display of this information in some other convenient form.

The foregoing is a description of the preferred embodiments of the present invention. However, the invention is not so limited. Various alterations and modifications will be readily apparent within the scope of the invention. Other uses for the monitoring apparatus and method will also be apparent. The invention is only limited by the claims appended hereto.

I claim:

1. A monitoring apparatus comprising: a tube and means for determining a position of the tube in a patient having;
    signal generator means for generating a plurality of signals, each signal having a predetermined frequency, wherein said signal generator means is operatively connected to said tube so that said plurality of signals are propagated into said tube;
    signal amplitude determining means for individually determining a signal amplitude for each of said plurality of signals;
    resonant frequency determining means responsive to said signal amplitude determining means for determining a resonant frequency of said tube:
    first memory means for storing the determined resonant frequency; and
    second memory means for storing a signal amplitude associated with said resonant frequency.

2. The monitoring apparatus of claim 1 wherein:
    said signal generator means continuously produces a measuring signal having a frequency substantially equal to said resonant frequency and said amplitude determining means determines a signal amplitude associated with said measuring signal, said monitoring apparatus further comprising:
    comparator means for comparing the signal amplitude associated with said measuring signal with a stored signal amplitude associated with said determined resonant frequency; and
    indicator means responsive to said comparator means for indicating a result of a comparison made by said comparator means.

3. The monitoring apparatus of claim 2 wherein said comparator means comprises:
    means for digitizing the signal amplitude associated with said measuring signal;
    digital comparator means for comparing the signal amplitude associated with said measuring signal and said stored signal amplitude associated with said resonant frequency; and
    wherein said indicator means comprises a digital display.

4. The monitoring apparatus of claim 3 wherein said comparator means compares the signal amplitude associated with said measuring signal by measuring a phase angle where said measuring signal crosses a preset threshold.

5. The monitoring apparatus of claim 4 wherein said indicator means comprises a multicolored light display that changes color when the phase angle is past a preset amount.

6. The monitoring apparatus of claim 4 wherein said digital display comprises means for displaying the phase angle.

7. The monitoring apparatus of claim 1 wherein said signal generator means comprises a sine wave generator.

8. The monitoring apparatus of claim 1 wherein said first memory means initially stores an initial resonant frequency and said monitoring apparatus further comprises:
    means for continually determining a new resonant frequency; and
    means for comparing said initial resonant frequency and new resonant frequency and displaying a difference between said resonant frequencies.

* * * * *